(12) United States Patent
Tesar et al.

(10) Patent No.: US 7,221,522 B2
(45) Date of Patent: May 22, 2007

(54) OPTICAL SYSTEM FOR VARIABLE DIRECTION OF VIEW INSTRUMENT

(75) Inventors: John C. Tesar, Tucson, AZ (US); Eric L. Hale, Altadena, CA (US); Nathan Jon Schara, Pasadena, CA (US); Hans David Hoeg, Arcadia, CA (US)

(73) Assignee: Karl Storz Development Corp., Goleta, CA (US)

( * ) Notice: Subject to any disclaimer, the term of this patent is extended or adjusted under 35 U.S.C. 154(b) by 0 days.

(21) Appl. No.: 11/342,387

(22) Filed: Jan. 27, 2006

(65) Prior Publication Data

US 2006/0256450 A1 Nov. 16, 2006

Related U.S. Application Data

(60) Provisional application No. 60/648,332, filed on Jan. 28, 2005.

(51) Int. Cl.
*G02B 9/00* (2006.01)
*G02B 5/04* (2006.01)
*G02B 23/24* (2006.01)

(52) U.S. Cl. .............. 359/740; 359/738; 359/739; 359/833; 359/362

(58) Field of Classification Search ........ 359/656–661, 359/726, 733–736, 738–740, 831, 833, 362
See application file for complete search history.

(56) References Cited

U.S. PATENT DOCUMENTS

| | | | |
|---|---|---|---|
| 3,880,148 A | 4/1975 | Kanehira et al. | 128/6 |
| 4,037,938 A | 7/1977 | Yamashita et al. | 350/202 |
| 4,042,295 A | 8/1977 | Yamasita et al. | 350/202 |
| 4,059,344 A | 11/1977 | Yamasita | 350/202 |
| 4,140,364 A | 2/1979 | Yamashita et al. | 350/26 |
| 4,354,734 A | 10/1982 | Nakahashi | 350/96.26 |
| 4,598,980 A | 7/1986 | Doi et al. | 350/445 |
| 4,662,725 A | 5/1987 | Nisioka | 350/432 |
| 4,697,577 A | 10/1987 | Forkner | 128/6 |
| 4,916,534 A * | 4/1990 | Takhashi et al. | 348/67 |

(Continued)

FOREIGN PATENT DOCUMENTS

DE  299 07 430  10/1999

(Continued)

OTHER PUBLICATIONS

Extended European Search Report; May 2, 2006; 6 pages.
Extended European Search Report ; Jun. 22, 2006; 7 pages.

*Primary Examiner*—Ricky Mack
*Assistant Examiner*—Jack Dinh
(74) *Attorney, Agent, or Firm*—St. Onge Steward Johnston & Reens LLC

(57) ABSTRACT

A optical system for a viewing instrument with a variable direction of view is disclosed generally comprising shaft, first and second reflectors located at the distal end of the shaft, where the first reflector rotates about an axis angularly offset from the longitudinal axis of the shaft, and an entrance pupil positioned in the optical path created by the reflectors and preceding the reflecting surface of the second reflector. In certain embodiments, the entrance pupil comprises an aperture stop positioned between the first and second reflectors. In some embodiments, the system includes negative and positive lenses located adjacent the entrance and exit faces of the first reflector.

35 Claims, 6 Drawing Sheets

U.S. PATENT DOCUMENTS

| | | | |
|---|---|---|---|
| 5,899,851 A | 5/1999 | Koninckx | 600/117 |
| 6,256,155 B1 | 7/2001 | Nagaoka | 359/753 |
| 6,522,906 B1 | 2/2003 | Salisbury, Jr. et al. | 600/407 |
| 6,560,013 B1 | 5/2003 | Ramsbottom | 359/431 |
| 6,648,817 B2 | 11/2003 | Schara et al. | 600/173 |
| 2004/0127769 A1 | 7/2004 | Hale et al. | 600/173 |
| 2005/0054895 A1 | 3/2005 | Hoeg et al. | 600/117 |

FOREIGN PATENT DOCUMENTS

| | | |
|---|---|---|
| WO | WO 98/46120 | 10/1998 |
| WO | WO 99/42028 | 8/1999 |
| WO | WO 01/22865 | 4/2001 |
| WO | 1 466 552 | 10/2004 |

\* cited by examiner

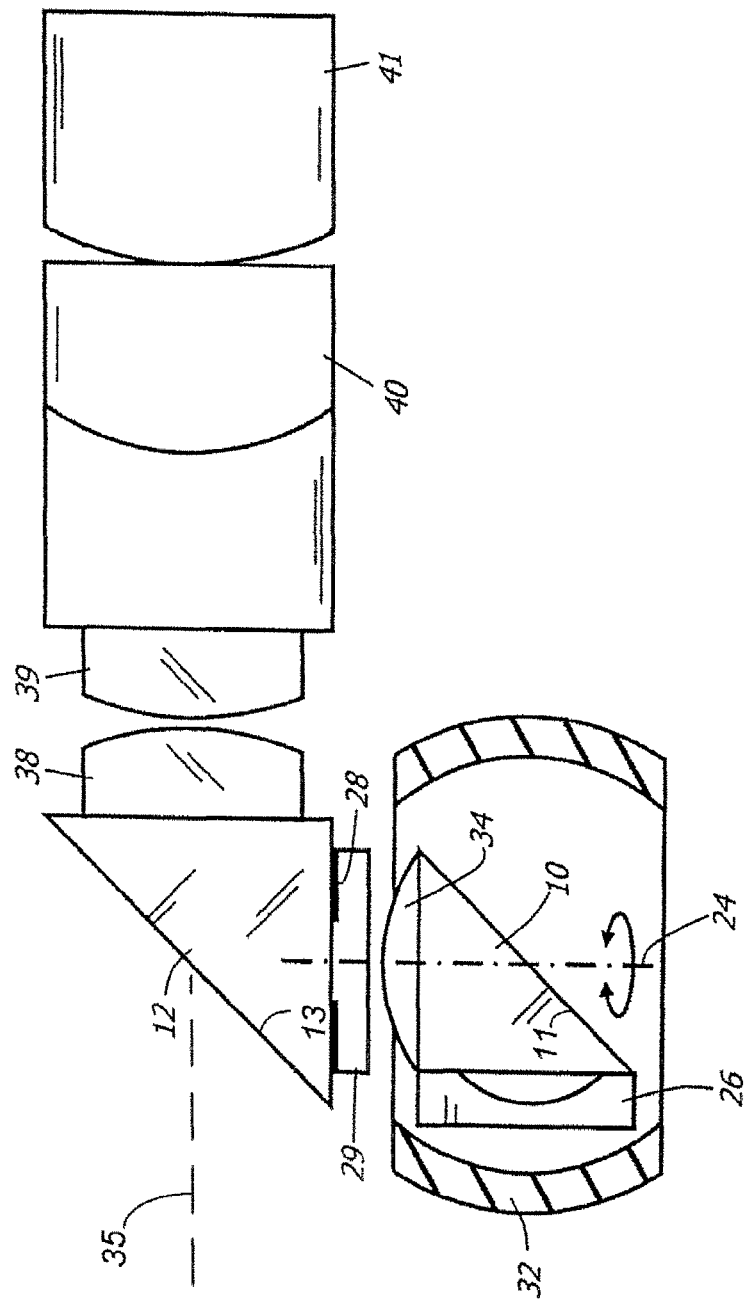

OPTICAL SYSTEM FOR VARIABLE DIRECTION OF VIEW INSTRUMENT

CROSS-REFERENCE TO RELATED APPLICATIONS

This patent application claims the benefit of, under Title 35, United States Code, Section 119(e), U.S. Provisional Patent Application No. 60/648,332, filed Jan. 28, 2005.

FIELD OF THE INVENTION

The present invention relates to an apparatus for obtaining wide angles of view in small areas, such as a surgical site in a patient's body. More specifically, the invention relates to an objective optical system for a viewing instrument, such as an endoscope, with a variable direction of view.

BACKGROUND OF THE INVENTION

Viewing instruments, such as endoscopes, are generally well known in the art. Generally, an endoscope is a medical device for insertion into a body passageway or cavity that enables an operator to view and/or perform certain surgical procedures at a site inside a patient's body. As is known, endoscopes may be either rigid or flexible, and generally include a long tubular member equipped with, for example, some type of system for transmitting images to the user, and in some cases, a working channel for a surgical instrument. The endoscope has a proximal end that remains external to the patient, from which the operator can view the site and/or manipulate a surgical instrument, and a distal end having an endoscope tip for insertion into the body cavity of the patient.

Generally, these instruments employ some form of objective lens system, which focuses the image onto some form of image guide, such as a fiber optic bundle or relay lenses, thereby transmitting the images from inside the body cavity of the patient to the user's eye located at the proximal end of the endoscope, or to a camera likewise connected to the scope for subsequent display on a monitor and/or storage on an image capture device. Generally, these objective optical systems attempt to simultaneously maximize the field of view, maximize the image quality, provide telecentric image transmission to the image guide, and minimize the size and cost of the system.

For example, U.S. Pat. No. 4,354,734 to Nakahashi discloses an objective optical system with a telecentric design that has been very effective in providing a wide field of view in a compact, low-cost assembly. A number of retrofocal optical systems have been proposed, such as those described in U.S. Pat. No. 4,037,938 to Yamashita et al., U.S. Pat. No. 4,042,295 to Yamashita et al., U.S. Pat. No. 4,059,344 to Yamashita, U.S. Pat. No. 4,662,725 to Nisioka, and U.S. Pat. No. 6,256,155 to Nagaoka. However, all of these disclosures pertain to objective systems for endoscopes that have fixed viewing directions, and are not appropriate with endoscopes having a variable direction of view.

The operating principles of such a variable direction of view scope are described in U.S. Patent Application No. 2005/0054895 by Hoeg, et al., the specification of which is hereby incorporated herein by reference. Generally, such a scope has a view vector with an attendant view field that has at least two degrees of freedom. The first degree of freedom permits rotation of the view vector about the longitudinal axis of the endoscope's shaft, which allows the view vector to scan in a latitudinal direction, while the second degree of freedom permits rotation of the view vector about an axis perpendicular to the scope's longitudinal axis, which allows the view vector to scan in a longitudinal direction. In some cases, a third degree of freedom is also be available.

A number of such variable direction of view scopes have been proposed that use adjacent fixed and variable prisms to provide the variable direction of view, such as, for example, the designs disclosed in U.S. Pat. No. 3,880,148 to Kanehira et al., U.S. Pat. No. 4,697,577 to Forkner, U.S. Pat. No. 6,648,817 to Schara et al., German Patent DE 299 07 430, WIPO Publication No. WO 99/42028 by Hoeg, WIPO Publication No. WO 01/22865 by Ramsbottom.

A typical example of a basic dual reflector system is illustrated schematically in FIG. 1A. A pivotable reflector 10, usually a prism, reflects received light to a fixed reflector 12, also a prism, which further reflects the light into an optical train 14 for transmission to the viewer. In this way, the reflectors 10, 12, define an optical path comprising three segments 16, 18, 20. A view vector 22 exists in coincidence with the first optical path segment 16. By rotating the pivotable prism 10 about a rotational axis 24 coincident with the second optical path segment 18, the view vector 22 can be swept around in a plane normal to the rotational axis 24 (i.e., normal to the page). Even though this design is optimally compact, the use of only the rotating and fixed prisms 10, 12 results in an unacceptably small field of the view and is not telecentric.

Therefore, improved versions of the basic dual reflector design, employing additional optical mechanisms for improving the field of view, have been proposed. An example of such a system is shown in FIG. 1B. As illustrated, the design involves a simple retrofocus arrangement having a negative lens 26, an aperture stop 28 placed on the reflective face of the fixed prism 12, and a positive lens group 30. While this design provides an improved field of view, it is still not telecentric, does not provide sufficient chromatic and geometric correction, and is not optimally compact, as evidenced by the increased size of the pivotable prism 10. Additionally, the increased prism size also causes the scanning range to be limited, as the rotating prism 10 would be obstructed by the lens group 30. Finally, the reflecting surface (i.e., hypotenuse) of the fixed prism 12 is not the optimal place for the aperture stop 28.

Therefore, a continuous challenge presented by these systems is producing a suitable objective optical system that adequately accommodates this sort of dual reflector design. At the same time, there remains, in addition to the performance of the particular objective system, the ever-present desire to minimize the space required by the optics, including both the rotating and non-rotating prisms, as well as any other elements employed, as it is generally desired to produce scope diameters that are as small as possible in order to facilitate insertion and retraction. Because a dual prism design, such as those noted above, entails the use of two prisms positioned side-by-side transverse to the longitudinal axis of the scope, the scope diameter is usually somewhat large.

Therefore, it is desirable to design the system in such a way that the size of the optics can be minimized, while still providing the advantages of telecentricity, a large scanning range, a large field of view, and good image quality in a cost-effective manner. To date, this has been difficult to accomplish, as these interests often conflict. For example, decreasing the size of the optical elements typically reduces the amount of light admitted by the system and adversely affects the image brightness. As another example, increasing the field of view typically exacerbates optical aberrations and degrades image quality.

One of many critical design parameters in the optical system of such instruments is the entrance pupil, which is the location where the diameter of the light beam is minimal. This is also the location where an aperture stop can be optimally located to best condition the image and control image brightness and other image quality parameters. Most of the proposed designs noted above do not even mention the existence of an entrance pupil or aperture stop anywhere in the optical systems, while the design of Ramsbottom, for instance, apparently has the entrance pupil and accompanying aperture stop at the reflective face of the fixed reflector. This is not ideal, as this location of the aperture stop negatively affects both system size and performance—the system should be designed to accommodate larger diameter light flow on either side of it.

What is desired, therefore, is an optical system for a variable direction of view instrument that maximizes the field of view. What is further desired is an optical system for a variable direction of view instrument that maximizes the image quality and provides telecentric image transmission to the image guide. What is also desired is an optical system for a variable direction of view instrument that minimizes both the size and cost of the instrument.

SUMMARY OF THE INVENTION

Accordingly, it is an object of the present invention to provide an optical system for a variable direction of view instrument that provides a large scanning range and field of view.

It is a further object of the present invention to provide an optical system for a variable direction of view instrument that does not employ a large reflector that unnecessarily increases the instrument diameter.

It is yet another object of the present invention to provide an optical system for a variable direction of view instrument that does not require an amount of optical elements that unnecessarily increases the instrument diameter.

It is still another object of the present invention to provide an optical system for a variable direction of view instrument that does not decrease the size of the optical elements so as to unnecessarily reduce the amount of admitted light and adversely affect image brightness.

It is yet another object of the present invention to provide an optical system for a variable direction of view instrument that provides telecentric image transmission.

In order to overcome the deficiencies of the prior art and to achieve at least some of the objects and advantages listed, the invention comprises a viewing instrument with a variable direction of view, including a shaft having a distal end and a longitudinal axis, first and second reflectors located at the distal end of the shaft for folding an optical path of incoming light, the first reflector having a rotational axis angularly offset from the longitudinal axis of the shaft about which the first reflector rotates, wherein the first reflector has a first reflecting surface that receives and redirects the incoming light towards the second reflector, and the second reflector has a second reflecting surface that redirects the light from the first reflector along the shaft, and an aperture stop located in the optical path and preceding the second reflecting surface.

In some of these embodiments, the first and second reflectors comprise first and second prisms.

In certain embodiments, the first reflector has an exit face through which the light redirected by the first reflecting surface exits the first reflector, the second reflector has an entrance face through which the light from the first reflector enters the second reflector, and the aperture stop is located between the exit face of the first reflector and the entrance face of the second reflector. In some of these embodiments, the aperture stop is located on the entrance face of the second reflector, while in some embodiments, the aperture stop is located on the exit face of the first reflector. In certain embodiments, the aperture stop is located on the first reflecting surface.

In some of these embodiments, a negative lens is located adjacent the first reflector through which the incoming light is transmitted to the first reflector, and a convex surface through which the light redirected by the first reflecting surface is transmitted to the second reflector.

In another embodiment, the invention comprises a viewing instrument with a variable direction of view, including a shaft having a distal end and a longitudinal axis, first and second reflectors located at the distal end of the shaft, the first reflector having a rotational axis angularly offset from the longitudinal axis of the shaft about which the first reflector rotates, the second reflector having a reflecting surface, and an optical path along which incoming light travels to the first reflector, is redirected by the first reflector towards the second reflector, and is redirected by the reflecting surface of the second reflector along the shaft, wherein the optical path includes an entrance pupil preceding the reflecting surface of the second reflector.

In yet another embodiment, the invention comprises a viewing instrument with a variable direction of view, including a shaft having a distal end and a longitudinal axis, first and second reflectors located at the distal end of the shaft, the first reflector having a rotational axis angularly offset from the longitudinal axis of the shaft about which the first reflector rotates, an optical train located in the shaft, and an optical path along which incoming light travels to the first reflector, is redirected by the first reflector towards the second reflector, and is redirected by the second reflector towards the optical train, wherein the optical path includes an entrance pupil preceding the second reflector.

BRIEF DESCRIPTION OF THE DRAWINGS

FIG. 2 is side view in partial cross-section of the optical system of a viewing instrument in accordance with the invention.

DETAILED DESCRIPTION OF THE INVENTION

Figure 1A:
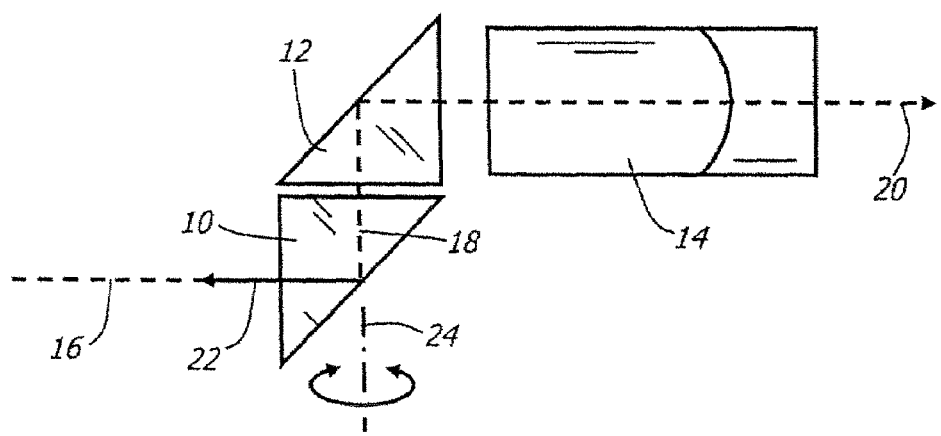
FIGS. 1A–B are side views of optical systems existing in the prior art.
Figure 1B:
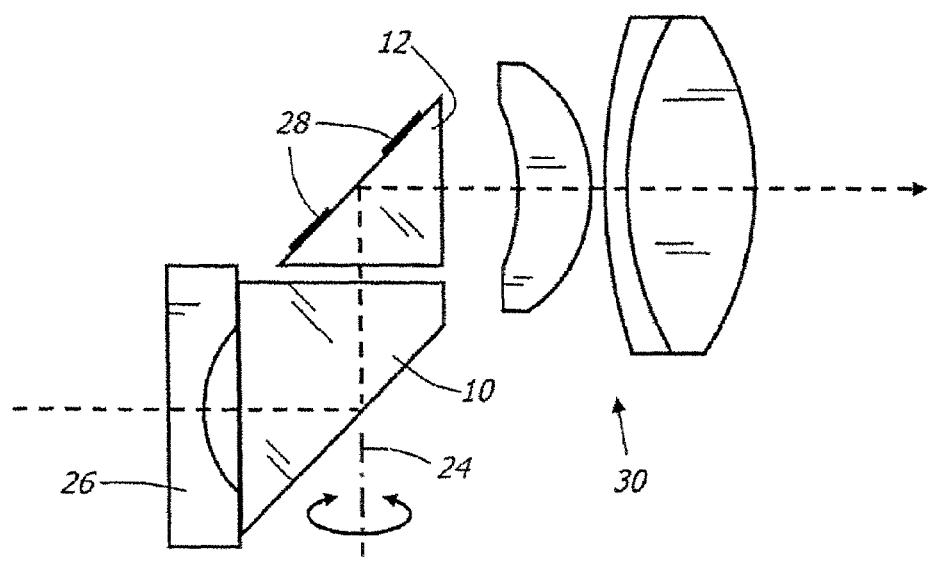

The basic components of one embodiment of a optical system for a variable direction of view instrument in accordance with the invention are illustrated in FIGS. 2–3. As used in the description, the terms "top," "bottom," "above," "below," "over," "under," "above," "beneath," "on top," "underneath," "up," "down," "upper," "lower," "front," "rear," "back," "forward" and "backward " refer to the objects referenced when in the orientation illustrated in the drawings, which orientation is not necessary for achieving the objects of the invention.

Referring to FIG. 2, and starting from the object side, this optical system comprises a spherical viewing window 32 with zero optical power (or as close to zero as current optical fabrication techniques will allow), a first lens 26 of negative refraction power, a first reflector 10, a second lens 34 of positive refractive power, an aperture stop 28 seated on the back of a mounting element 29 (which could be constructed with a weak positive optical power), a second reflector 12, a set of third and fourth lenses 38, 39 of positive refractive power, a doublet 40 and a field lens 41 of positive refractive power.

The first reflector may comprise a prism 10 that rotates about a rotational axis 24, which in certain advantageous embodiments, is substantially perpendicular to the longitudinal axis 35 of the shaft 33. The prism 10 has a first reflecting surface 11 that redirects incoming light to the second reflector which may comprise a fixed prism 12. The second prism 12, in turn, has a second reflecting surface 13 that redirects the light from the first reflector 10 to the optical train 38, 39, 40, 41 in the shaft. Additionally, though the positive lens 34 has been shown as a separate, plano-convex lens, other configurations are possible, such as, for example a convex surface comprising the exit face of the first prism 10. Similarly, other configurations for the optical train 38, 39, 40, 41 are possible.

Figure 3A:
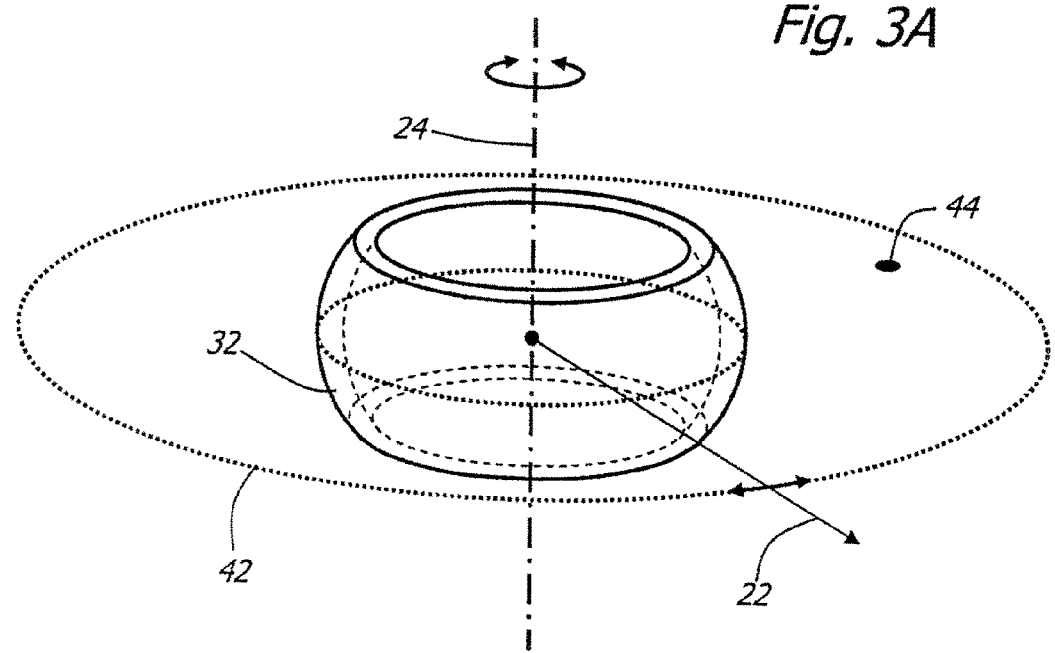
FIG. 3A is a side isometric view of the viewing window of the optical system of FIG. 2.
Figure 3B:
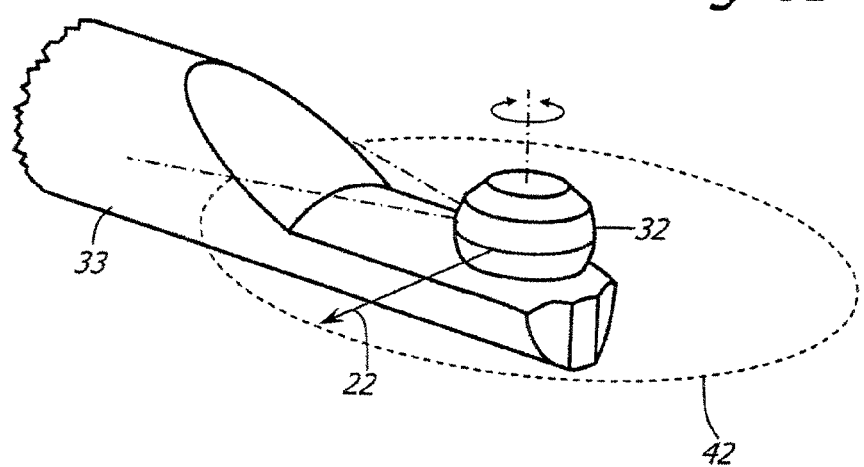
FIG. 3B is an isometric view of a portion of a viewing instrument employing the optical system of FIG. 2.

The viewing window 32 is illustrated in detail in FIGS. 3A–B. The window 32, which seals the optical system against fluid and debris, is basically a surface of revolution about the rotational axis 24 and comprises a layer of rigid material, such as glass or sapphire. The window 32 is generally symmetric about a scan plane 44 of the view vector 22 and, due to its shape, the window 32 allows the view vector 22 to rotate fully through the scan plane 44, thereby sweeping out a 360 degree viewing range 42.

The window 32 has a general sphericity that helps minimize distortion and other image-degrading effects, as the chief light rays entering the optical system via the window 32 will be generally normal to the outer surface thereof, and thus, will suffer minimal refraction. Because of the spherical shape of the window 32, this condition can be maintained throughout a full 360 degree sweep. It should be noted, however, that in certain other embodiments, in may be desirable to use other window shapes, such as, for example, cylindrical.

Figure 4A:
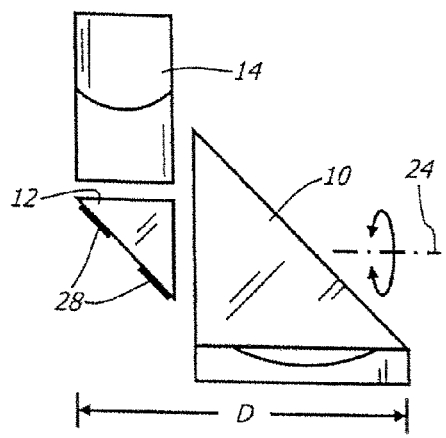
FIG. 4A is a side view of an optical system existing in the prior art.
Figure 4B:
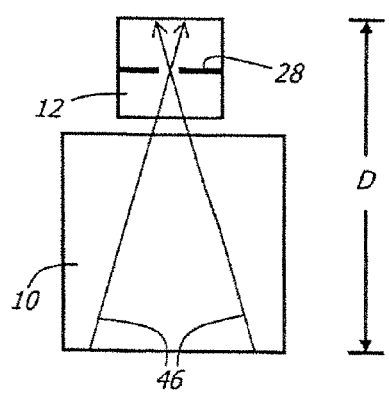
FIG. 4B is a schematic view of the unfolded optical path of the optical system of FIG. 4A.

FIGS. 4A–F show system geometries and fields of view for different entrance pupils and accompanying aperture stops for a given diameter. Referring first to FIGS. 4A–B, the aperture stop 28 is located on the reflective surface of the fixed prism 12 (which has been suggested in the prior art). As mentioned, this entrance pupil has inherent problems, and it does not make optimal use of available space. This is demonstrated by the schematic of the unfolded optical path in FIG. 4B, which shows the pivotable prism 10 and the fixed prism 12 represented as squares being traversed by a set of limit rays 46. The location of the aperture stop 28 forces the rotating prism 10 to be large in order to accommodate the optical path, thus limiting either the swing range of the pivotable prism 10 or the size and throughput of the optical train 14. The increased size of the prism 10 also causes it to sweep out a larger volume, necessitating a larger viewing window 32. Moreover, since the objective system should be telecentric, the optical train 14 does not need to have a diameter larger than the lateral face of the fixed prism 12, and thus, will typically be limited to this diameter in order to minimize space where possible in order to limit the overall diameter of the instrument, even though this decrease in the size of the optical elements unfortunately reduces the amount of admitted light and adversely affects image brightness.

Figure 4C:
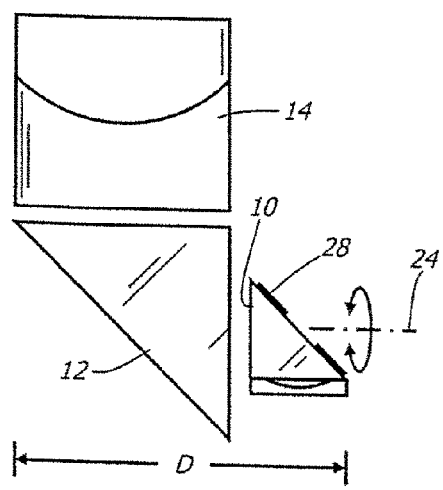
FIG. 4C is a side view showing additional detail of the optical system of FIG. 2.
Figure 4D:
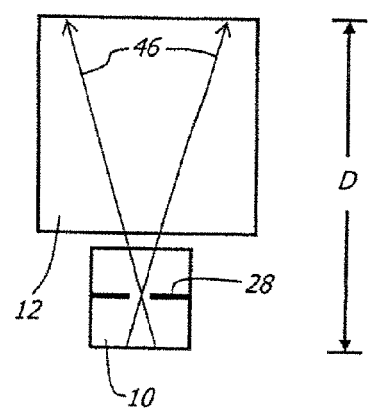
FIG. 4D is a schematic view of the unfolded optical path of the optical system of FIG. 4C.

Accordingly, as shown in FIGS. 4C–D, in certain advantageous embodiments of the invention, the aperture stop 28 is located on the reflective surface of the rotatable prism 10. This location requires a larger fixed prism 12 in order to maintain the field of view, but it allows a minimal pivotable prism 10. Therefore, the overall space required is shifted more towards the fixed prism 12, allowing a maximum diameter optical train 14.

Figure 4E:
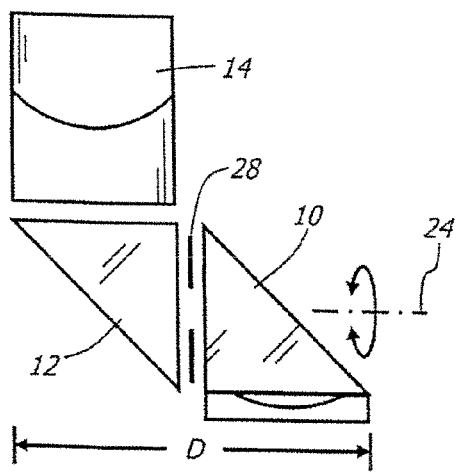
FIG. 4E is a side view showing additional detail of the optical system of FIG. 2.
Figure 4F:
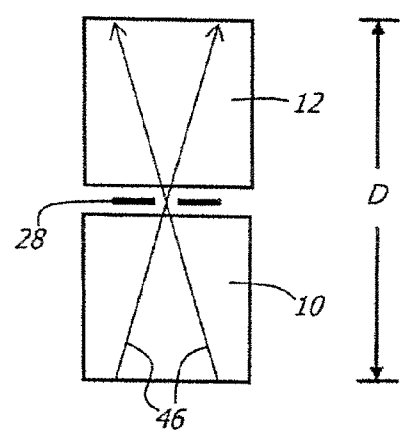
FIG. 4F is a schematic view of the unfolded optical path of the optical system of FIG. 4E.

Alternatively, because there is a limit on how small the pivotable prism 10 can be made, and also in order to not locate the entrance pupil on a reflective surface, in some advantageous embodiments, the aperture stop 28 is located between the exit face of the prism 10 and the entrance face of the prism 12. Accordingly, the stop 28 may be positioned on an opposing face of the prisms 10, 12, or in between these faces, as shown in FIGS. 4E–F. This allows both prisms 10, 12 to be the same size, yielding the smallest overall diameter. By positioning the entrance pupil in the optical path at a point preceding the reflecting surface of the second prism 12 in this way, image quality can be maintained while minimizing the instrument diameter.

Figure 5:
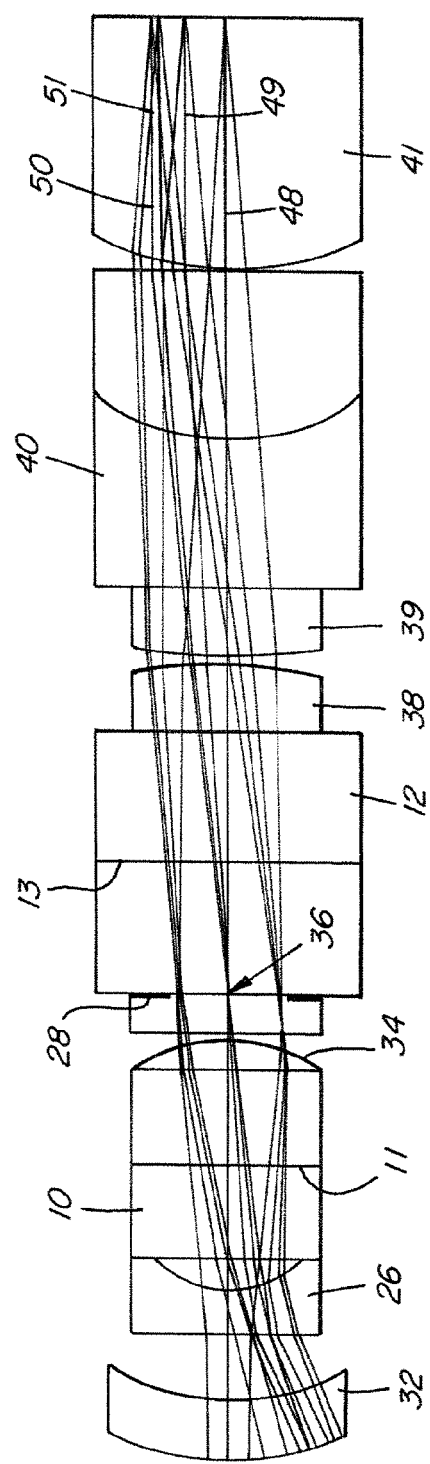
FIG. 5 is a schematic view of the unfolded optical paths produced by the optical system of FIG. 2.

FIG. 5 shows the unfolded optical paths for blue, green, yellow, and red principal rays 48, 49, 50, 51 through the objective lens system illustrated in FIG. 2. The first lens 26 "condenses" the optical field for passage through the pivotable prism 10, shown unfolded with the optical folding plane 11 indicated. This arrangement yields a wide field of the view while also allowing a smaller diameter optical relay system. The principal rays 48, 49, 50, 51 have an intersection point 36 at the interface between the mounting element 29 and the fixed prism 12 (with folding plane 13). The series of lenses 38, 39, 40 and 41 condition the optical signal for maximal image performance (resolution, contrast, depth of field, distortion, modulation transfer function) before an image is formed on the exit face of the field lens 41, at which point the chief rays 48, 49, 50 and 51 are parallel. This telecentric quality of the objective system minimizes the transmission loss as light leaves the objective system and travels into the image guide (not shown). In this way, the invention provides a retrofocal telecentric objective optical system for dual prism variable direction of view endoscopes, featuring a compact design which delivers high image quality, continuous 360 degree viewing, and an acceptably large field of view.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A viewing instrument with a variable direction of view, comprising:
   a shaft having a distal end and a longitudinal axis;
   first and second reflectors located at the distal end of said shaft for folding an optical path of incoming light, said first reflector having a rotational axis angularly offset from the longitudinal axis of said shaft about which said first reflector rotates;
   wherein said first reflector has a first reflecting surface that receives and redirects the incoming light towards said second reflector, and said second reflector has a second reflecting surface that redirects the light from said first reflector along said shaft;
   a convex surface through which the light redirected by said first reflecting surface is transmitted to said second reflector; and
   an aperture stop located in the optical path between said convex surface and said second reflecting surface.

2. The viewing instrument of claim 1, wherein the rotational axis of said first reflector is substantially perpendicular to the longitudinal axis of said shaft.

3. The viewing instrument of claim 1, wherein:
   said second reflector has an entrance face through which the light from said first reflector enters said second reflector; and
   said aperture stop is located on the entrance face of said second reflector.

4. The viewing instrument of claim 1, wherein said first and second reflectors comprise first and second prisms.

5. The viewing instrument of claim 1, further comprising:
   a negative lens located adjacent said first reflector through which the incoming light is transmitted to said first reflector.

6. The viewing instrument of claim 5, wherein said negative lens has an optical axis substantially perpendicular to said rotational axis.

7. The viewing instrument of claim 1, wherein said convex surface comprises an outer surface of said first reflector.

8. The viewing instrument of claim 1, further comprising a positive lens located adjacent said first reflector, wherein said positive lens includes said convex surface.

9. The viewing instrument of claim 8, wherein said positive lens comprises a piano-convex lens.

10. The viewing instrument of claim 1, further comprising an optical train disposed in said shaft for receiving and transmitting the light redirected by said second reflecting surface.

11. The viewing instrument of claim 10, wherein said optical train includes a plurality of positive lenses.

12. The viewing instrument of claim 1, further comprising a viewing window covering said first reflector.

13. The viewing instrument of claim 12, wherein said viewing window comprises a translucent surface of revolution generally symmetric about said rotational axis.

14. The viewing instrument of claim 1, wherein said shaft is an endoscope shaft.

15. A viewing instrument with a variable direction of view, comprising:
   a shaft having a distal end and a longitudinal axis;
   first and second reflectors located at the distal end of said shaft, said first reflector having a first reflecting surface and a rotational axis angularly offset from the longitudinal axis of said shaft about which said first reflector rotates, said second reflector having a second reflecting surface; and
   a convex surface between said first reflecting surface and said second reflecting surface;
   an optical path along which incoming light travels to said first reflector, is redirected by said first reflector through said convex surface towards said second reflector, and is redirected by said second reflecting surface along said shaft;
   wherein said optical path includes an entrance pupil between said convex surface and said second reflecting surface of said second reflector.

16. The viewing instrument of claim 15, wherein the rotational axis of said first reflector is substantially perpendicular to the longitudinal axis of said shaft.

17. The viewing instrument of claim 15, further comprising an aperture stop positioned in said optical path, wherein said entrance pupil is defined by said aperture stop.

18. The viewing instrument of claim 15, wherein:
   said second reflector has an entrance face through which the light from said first reflector enters said second reflector; and
   the entrance pupil of said optical path is located at the entrance face of said second reflector.

19. The viewing instrument of claim 15, wherein said first and second reflectors comprise first and second prisms.

20. The viewing instrument of claim 15, further comprising:
   a negative lens located adjacent said first reflector through which the incoming light is transmitted to said first reflector.

21. The viewing instrument of claim 20, wherein said negative lens has an optical axis substantially perpendicular to said rotational axis.

22. The viewing instrument of claim 15, wherein said convex surface comprises an outer surface of said first reflector.

23. The viewing instrument of claim 15, further comprising a positive lens located adjacent said first reflector, wherein said positive lens includes said convex surface.

24. The viewing instrument of claim 23, wherein said positive lens comprises a piano-convex lens.

25. The viewing instrument of claim 15, further comprising an optical train disposed in said shaft for receiving and transmitting the light redirected by said second reflecting surface.

26. The viewing instrument of claim 25, wherein said optical train includes a plurality of positive lenses.

27. The viewing instrument of claim 15, further comprising a viewing window covering said first reflector.

28. The viewing instrument of claim 27, wherein said viewing window comprises a translucent surface of revolution generally symmetric about said rotational axis.

29. The viewing instrument of claim 15, wherein said shaft is an endoscope shaft.

30. A viewing instrument with a variable direction of view, comprising:
   a shaft having a distal end and a longitudinal axis;
   first and second reflectors located at the distal end of said shaft, said first reflector having a rotational axis angularly offset from the longitudinal axis of said shaft about which said first reflector rotates;
   a convex lens surface located at the distal end of said shaft;
   an optical train located in said shaft; and
   an optical path along which incoming light travels to said first reflector, is redirected by said first reflector through said convex lens surface towards said second reflector, and is redirected by said second reflector towards said optical train;
wherein said optical path includes an entrance pupil between said convex surface and said second reflector.

31. The viewing instrument of claim 30, wherein said convex lens surface comprises an outer surface of said first reflector.

32. The viewing instrument of claim 30, further comprising a positive lens located adjacent said first reflector, wherein said positive lens includes said convex lens surface.

33. The viewing instrument of claim 32, wherein said first and second reflectors comprise first and second prisms.

34. The viewing instrument of claim 32, further comprising a negative lens located adjacent said first reflector through which the incoming light is transmitted to said first reflector.

35. The viewing instrument of claim 32, wherein said optical train includes a plurality of positive lenses.

* * * * *